United States Patent
Addy et al.

(10) Patent No.: US 6,594,971 B1
(45) Date of Patent: Jul. 22, 2003

(54) STERILE PACKAGING FOR FLEXIBLE ENDOSCOPES

(75) Inventors: Tralance Addy, Trabuco Canyon, CA (US); Su Syin Wu, Irvine, CA (US); Debra Timm, Foothill Ranch, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/474,141

(22) Filed: Dec. 29, 1999

Related U.S. Application Data (60) Provisional application No. 60/114,288, filed on Dec. 30, 1998.

(51) Int. Cl.[7] .......................... B65B 61/14; B65B 55/18
(52) U.S. Cl. .......................... 53/413; 53/425; 53/433; 53/434
(58) Field of Search .................. 53/425, 413, 432–434, 53/510–512, 134.1, 134.2, 167; 206/363, 438, 439, 571, 806; 383/7–10, 22–24; 422/26–28, 33, 40

(56) References Cited

U.S. PATENT DOCUMENTS

| | | | |
|---|---|---|---|
| 3,690,315 A | * | 9/1972 | Chittenden et al. ......... 206/363 |
| 3,814,901 A | | 6/1974 | Morhack |
| 3,926,309 A | | 12/1975 | Center |
| 3,939,971 A | | 2/1976 | Tulis |
| 3,946,871 A | | 3/1976 | Sturm |
| 4,149,650 A | | 4/1979 | Whelchel et al. |
| 4,203,943 A | | 5/1980 | Gillis et al. |
| 4,321,232 A | | 3/1982 | Bithell |
| 4,337,223 A | | 6/1982 | Kaye |
| 4,380,530 A | | 4/1983 | Kaye |
| 4,410,492 A | | 10/1983 | Kaye |
| 4,482,053 A | | 11/1984 | Alpern et al. |
| 4,526,622 A | | 7/1985 | Takamura et al. |
| 4,526,623 A | | 7/1985 | Ishii et al. |
| 4,573,576 A | * | 3/1986 | Krol ............................ 206/438 |
| 4,576,650 A | | 3/1986 | Yabe et al. |
| 4,576,792 A | | 3/1986 | Martensson |
| 4,579,597 A | | 4/1986 | Sasa et al. |
| 4,579,598 A | | 4/1986 | Sasa et al. |
| 4,596,696 A | | 6/1986 | Scoville, Jr. |
| 4,617,178 A | | 10/1986 | Nichols |
| 4,661,326 A | | 4/1987 | Schainholz |
| 4,671,943 A | | 6/1987 | Wahlquist |
| 4,731,222 A | | 3/1988 | Kralovic et al. |
| 4,744,951 A | | 5/1988 | Cummings et al. |
| 4,754,877 A | | 7/1988 | Johansson et al. |
| 4,756,882 A | | 7/1988 | Jacobs et al. |
| 4,781,471 A | * | 11/1988 | Sengewald ..................... 383/7 |

(List continued on next page.)

FOREIGN PATENT DOCUMENTS

DE           3416743 A1     7/1985

OTHER PUBLICATIONS

PCT International Search Report International Application No. PCT/US99/31101 dated Apr. 13, 2000.

*Primary Examiner*—Stephen F. Gerrity (57) ABSTRACT

A packaging enclosure for receiving a flexible endoscope during a sterilization procedure and sterile storage thereafter has a portion thereof which is semi-permeable. Provision is made for hanging the packaging enclosure over a hook or peg. In one embodiment the packaging enclosure conforms to the endoscope so that its two flexible portions may hang over opposite sides of the hook. Alternatively, a hook or aperture may be provided on the packaging enclosure for hanging it over the hook.

10 Claims, 7 Drawing Sheets

U.S. PATENT DOCUMENTS

| | | | |
|---|---|---|---|
| 4,783,321 A | 11/1988 | Spence | |
| 4,798,292 A | 1/1989 | Hauze | |
| 4,874,090 A | 10/1989 | Dyke | |
| 4,892,706 A | 1/1990 | Kralovic et al. | |
| 4,937,046 A | 6/1990 | Andersen et al. | |
| 4,943,414 A | 7/1990 | Jacobs et al. | |
| 4,956,145 A | 9/1990 | Cummings et al. | |
| 4,997,084 A | * 3/1991 | Opie et al. | 206/438 |
| 5,017,241 A | 5/1991 | Ryan | |
| 5,037,623 A | 8/1991 | Schneider et al. | |
| 5,077,008 A | 12/1991 | Kralovic et al. | |
| 5,091,343 A | 2/1992 | Schneider et al. | |
| 5,114,596 A | 5/1992 | Laterra | |
| 5,116,575 A | 5/1992 | Badertscher et al. | |
| 5,178,282 A | * 1/1993 | Williams | 206/363 |
| 5,186,893 A | 2/1993 | Moulton et al. | |
| 5,209,909 A | 5/1993 | Siegal et al. | |
| 5,217,698 A | 6/1993 | Siegel et al. | |
| 5,222,600 A | 6/1993 | Stoddard et al. | |
| 5,225,160 A | 7/1993 | Sanford et al. | |
| 5,260,021 A | 11/1993 | Zeleznick | |
| 5,266,275 A | 11/1993 | Faddis | |
| 5,279,799 A | 1/1994 | Moser | |
| 5,310,524 A | 5/1994 | Campbell et al. | |
| 5,315,985 A | * 5/1994 | Decarie et al. | 600/101 |
| 5,348,711 A | 9/1994 | Johnson et al. | |
| 5,350,563 A | 9/1994 | Kralovic et al. | |
| 5,372,787 A | 12/1994 | Ritter | |
| 5,374,394 A | 12/1994 | Kralovic | |
| 5,391,360 A | 2/1995 | Kochte et al. | |
| 5,392,918 A | * 2/1995 | Harrison | 206/438 |
| 5,407,648 A | 4/1995 | Allen et al. | |
| 5,407,685 A | 4/1995 | Malchesky et al. | |
| 5,415,287 A | * 5/1995 | Hamano et al. | 206/363 |
| 5,418,022 A | * 5/1995 | Anderson et al. | 206/439 |
| 5,441,707 A | 8/1995 | Lewis et al. | |
| 5,443,801 A | 8/1995 | Langford | |
| 5,445,792 A | 8/1995 | Rickloff et al. | |
| 5,489,022 A | * 2/1996 | Baker | 53/425 |
| 5,490,975 A | 2/1996 | Dane | |
| 5,492,671 A | 2/1996 | Krafft | |
| 5,494,530 A | 2/1996 | Graf | |
| 5,505,218 A | 4/1996 | Steinhauser et al. | |
| 5,508,009 A | 4/1996 | Rickloff et al. | |
| 5,526,928 A | * 6/1996 | Yabe et al. | 206/363 |
| 5,527,508 A | 6/1996 | Childers et al. | |
| 5,534,221 A | 7/1996 | Hillebrenner et al. | |
| 5,540,901 A | 7/1996 | Riley | |
| 5,549,388 A | 8/1996 | Wilkes | |
| 5,552,115 A | 9/1996 | Malchesky | |
| 5,556,607 A | 9/1996 | Childers et al. | |
| 5,580,530 A | 12/1996 | Kowatsch et al. | |
| 5,609,821 A | 3/1997 | Grimberg et al. | |
| 5,638,661 A | 6/1997 | Banks | |
| 5,653,090 A | * 8/1997 | Weiss et al. | 53/425 |
| 5,667,068 A | 9/1997 | Weaver | |
| 5,697,887 A | * 12/1997 | Yabe et al. | 600/121 |
| 5,711,921 A | 1/1998 | Langford | |
| 5,715,943 A | 2/1998 | Thompson, Jr. | |
| 5,784,468 A | 7/1998 | Klayman | |
| 5,830,547 A | 11/1998 | MacKenzie et al. | |
| 5,868,244 A | * 2/1999 | Ivanov et al. | 53/425 |
| 5,947,296 A | * 9/1999 | Castora | 206/438 |

* cited by examiner

STERILE PACKAGING FOR FLEXIBLE ENDOSCOPES

This application claims priority from U.S. Ser. No. 60/114,288 filed Dec. 30, 1998.

FIELD

The present invention is directed to the field of coverings used to cover medical instruments during sterilization and in storage thereafter.

BACKGROUND

An endoscope typically comprises two flexible tubes connected to a body. One of the tubes is for insertion into a bodily orifice and the other typically connects to a light source. After a cleaning of an endoscope such as a sigmoidoscope or colonoscope, the endoscope is typically hung over a peg with the two flexible tubes hanging to opposite sides of the peg. This allows the flexible tubes to hang in a straight configuration. Due to the delicate nature of the fiber-optics in such tubes it is not recommended to coil them for storage.

A typical endoscope configuration comprises a small rigid control section connected to two flexible tubes. One tube comprises an insertion tube that contains a fiber-optic bundle and is usually covered with a sheath of polyurethane or other biocompatible material and contains a bending section that allows articulation or angulation of the insertion tube within human cavities. Connected to the control head, and hanging on the other side, is a universal cord that also contains a fiber-optic bundle and an air-water channel.

In a sterilization procedure, instruments are typically placed into a sterile barrier having a semi-permeable membrane. One popular form thereof comprises a pouch having at least one layer of a semi-permeable polymer such as TYVEK (registered trademark of E.I. duPont de Nemours Co., Inc.) brand polyethylene nonwoven fabric and a second layer which may comprise a layer of clear impermeable polymer or another layer of the same or a different semi-permeable polymer. The two layers are sealed together at their edges to enclose an instrument. Such pouches are typically rectangular in shape. Such a system allows sterilizing gases, such as hydrogen peroxide vapor, ethylene oxide or steam, to pass through the semi-permeable barrier to effect sterilization of the instrument therein but prevent microorganisms from entering the pouch after the sterilization process is complete thus allowing storage of the instrument in the packaging enclosure in a sterile manner. Those of skill in the art will recognize that many alternative package designs accomplish a similar function. For instance, such packages may comprise a layer of foam or other material which is rigid or semi-rigid and which may or may not be semi-permeable. The package may merely contain a small window or several small windows of semi-permeable material to allow sterilizing gases to enter.

Endoscopes such as sigmoidoscopes or colonoscopes have previously been only disinfected and the peg storage system was acceptable in such condition. Many users now demand that such instruments be sterilized, not merely subjected to a high level disinfection. The preferred barrier packaging enclosure for sterilization is a pouch, such as the aforementioned pouch, with heat or adhesive sealed boundaries that provides a sterile barrier with mechanical integrity, thereby preserving the sterility of the endoscope during storage of the endoscope after the sterilization procedure. However, such known pouches place the two flexible tubes of the endoscope together in a coiled pattern, and provide no method for storing a sterilized endoscope in an uncoiled or bent configuration. Some operators have even removed sterile endoscopes from rectangular pouches or other barrier systems to hang them on their old peg systems, thus compromising sterility.

SUMMARY OF THE INVENTION

The present invention overcomes these limitations to provide a sterile package which allows an endoscope to be sterilized therein and subsequently be stored in an uncoiled configuration by hanging over a peg while still in the package.

A packaging enclosure according to the present invention packages a flexible endoscope having first and second flexible tubes. The packaging enclosure comprises a wall forming an interior space impervious to microorganisms for receiving the endoscope. At least a portion of the wall is semi-permeable. A hanging means is provided for hanging the packaging enclosure, with the endoscope therein, over a hook.

Preferably, the packaging enclosure comprises a pouch having first and second films adhered to each other to form the interior space. The hanging means can comprise an aperture in the packaging enclosure. Alternatively, the hanging means can comprise the first flexible tube being receivable within one portion of the packaging enclosure and the second flexible tube being receivable within a second portion of the packaging enclosure and the packaging enclosure with the endoscope therein being drapable over the hook.

In one embodiment, the packaging enclosure comprises a thermoformed tray covered with a permeable lidstock. Preferably, one side of the pouch or the entire lidstock of the tray is formed of a semi-permeable material pervious to sterilizing gases yet impervious to microorganisms. However, such pouch side or lidstock may merely have one or more semi-permeable ports.

A method according to the invention for sterilizing and storing an endoscope having first and second flexible tubes is also provided. The method comprises the steps of:

placing the endoscope within a packaging enclosure comprising a wall forming an interior space for receiving the endoscope, at least a portion of the wall being semi-permeable;

passing a sterilizing gas into the packaging enclosure; and hanging the packaging enclosure with the sterile endoscope therein over a hook.

DETAILED DESCRIPTION

Figures 1, 2:
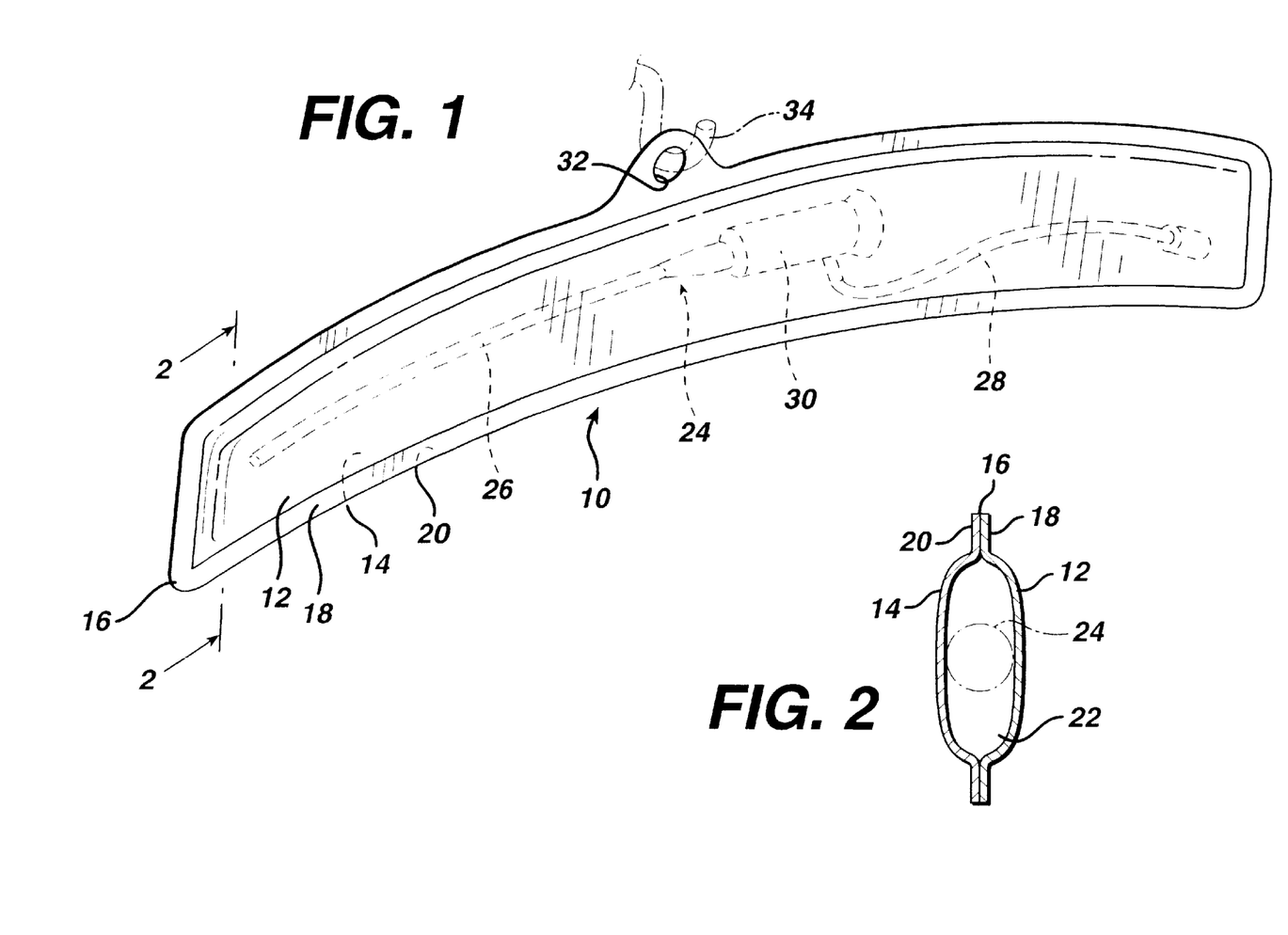
FIG. 1 shows a perspective view of a first embodiment of a packaging enclosure according to the invention.
FIG. 2 is a section view taken along lines 2—2 of FIG. 1.

FIGS. 1 and 2 illustrate an elongated pouch 10 having a front film 12 of a clear impermeable polymer and a rear film 14 of a semi-permeable material such as TYVEK brand nonwoven polyethylene fabric or a medical grade paper. An adhesive seal 16 about the outer edges 18 and 20 of the front film and rear film respectively forms a sealed interior space 22. The interior space 22 contains an endoscope 24 having a first flexible tube 26 and second flexible tube 28 attached to a body 30. A portion of the edges 18 and 20 is expanded and contains an aperture 32 therethrough whereby the pouch 10 can be hung on a hook 34. The elongated pouch 10, would also allow the pouch 10 to merely be draped over the hook 34 as is conventional for endoscopes not in pouches.

Figures 3, 4:
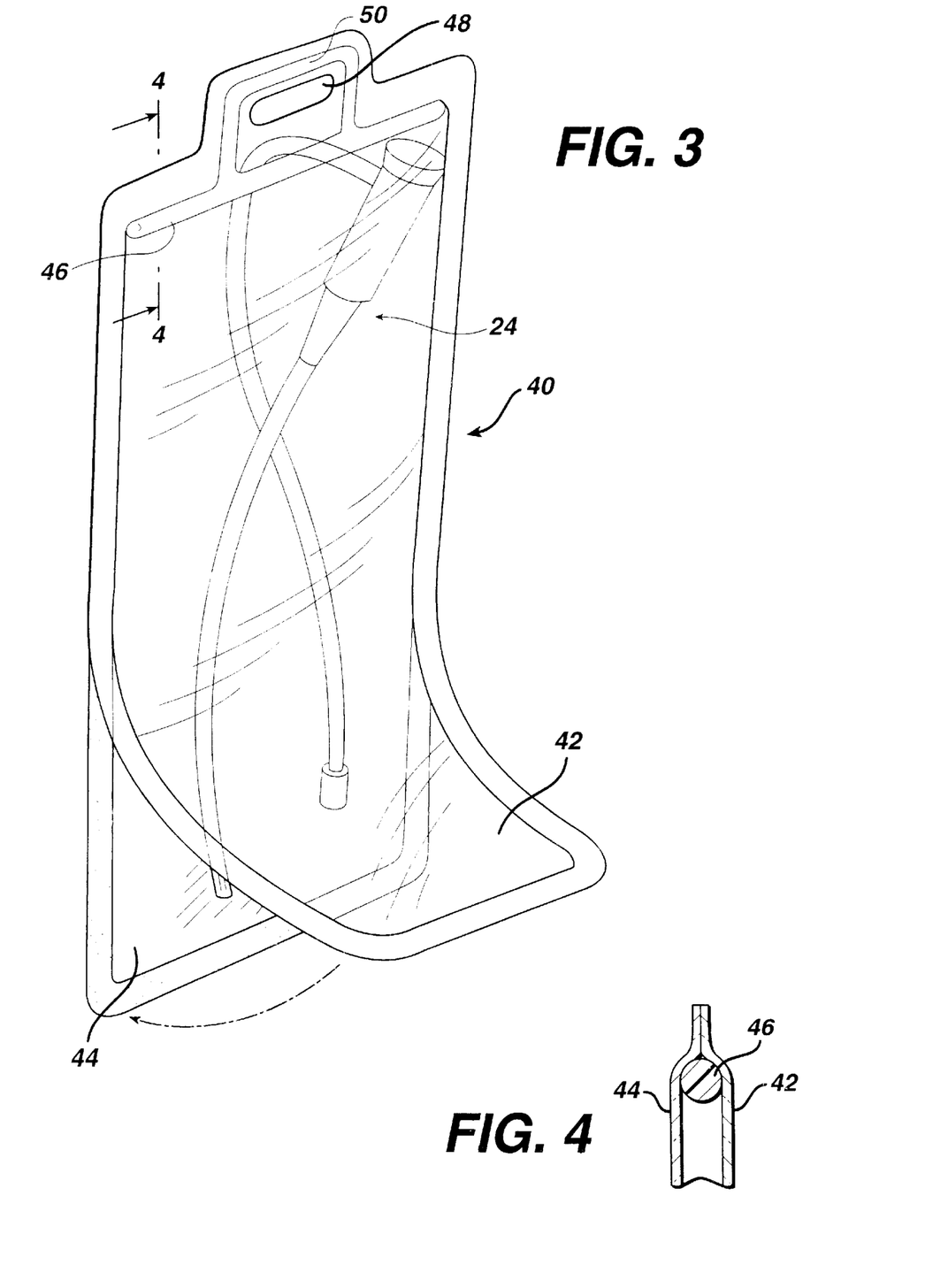
FIG. 3 is a perspective view of a second embodiment of a packaging enclosure according to the invention.
FIG. 4 is a section view taken along lines 4—4 of FIG. 3.

FIG. 3 illustrates a further embodiment in which a pouch 40 in which a front film 42 and rear film 44 are not elongated. However, a support member 46, preferably a rigid polymer, is formed into the pouch 40 and allows the endoscope 24 to hang thereover within the pouch 40. The pouch has an aperture 48 for hanging and the support member 46 has a reinforcing loop 50 which extends around the aperture 48 so as to provide additional strength.

Figure 5:
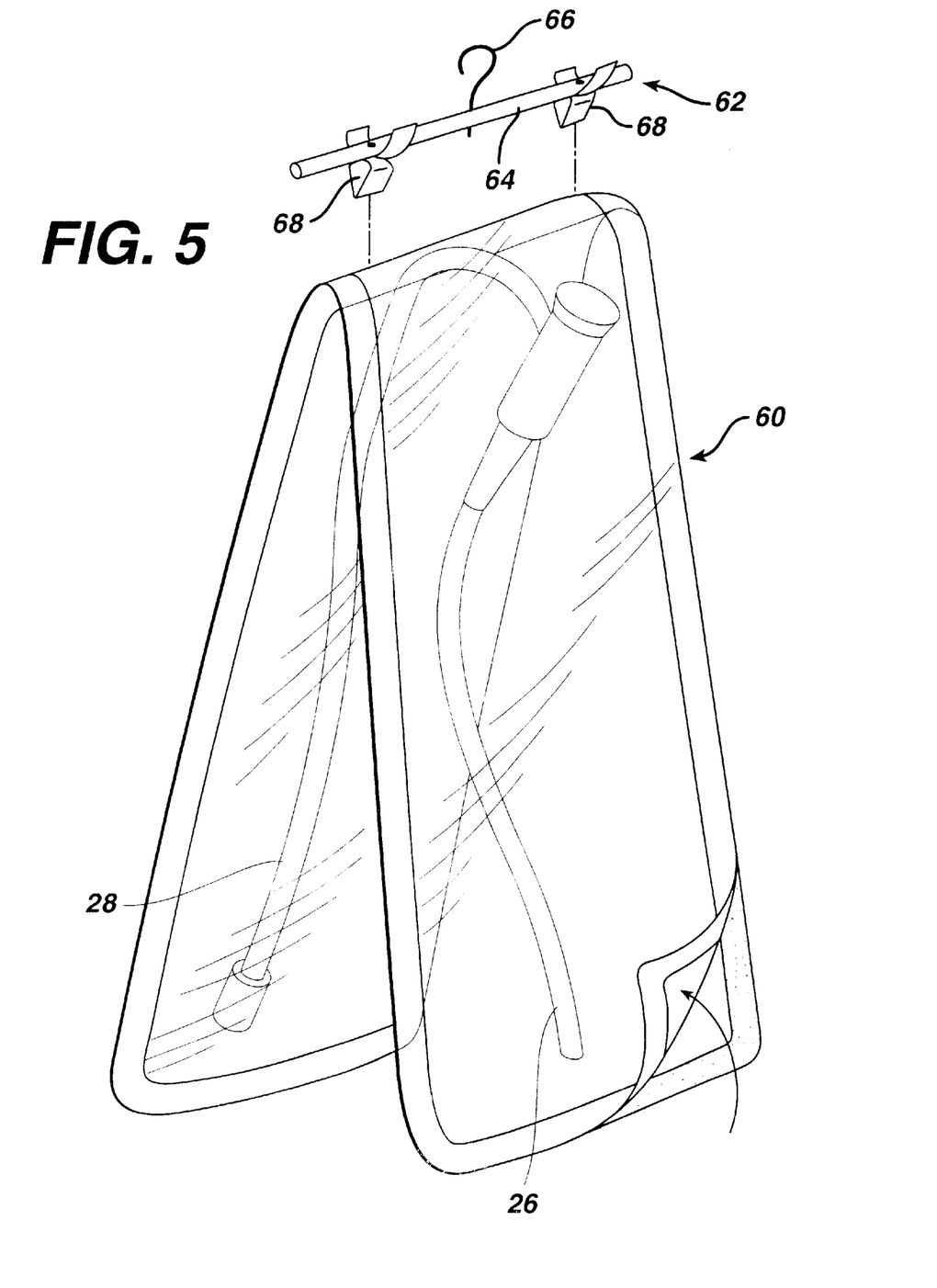
FIG. 5 is a perspective view of a third embodiment of a packaging enclosure according to the invention.

FIG. 5 shows an elongated pouch 60 which allows the first and second endoscope flexible tubes 26 and 28 to be separate to allow draping of the pouch 60 with the endoscope therein over a peg or hook (not shown in FIG. 5). Additionally, a separate hanger 62 with a support bar 64 with an upstanding central hook 66 and two depending clips 68 is provided for hanging the pouch 60 with the endoscope therein.

Figure 6:
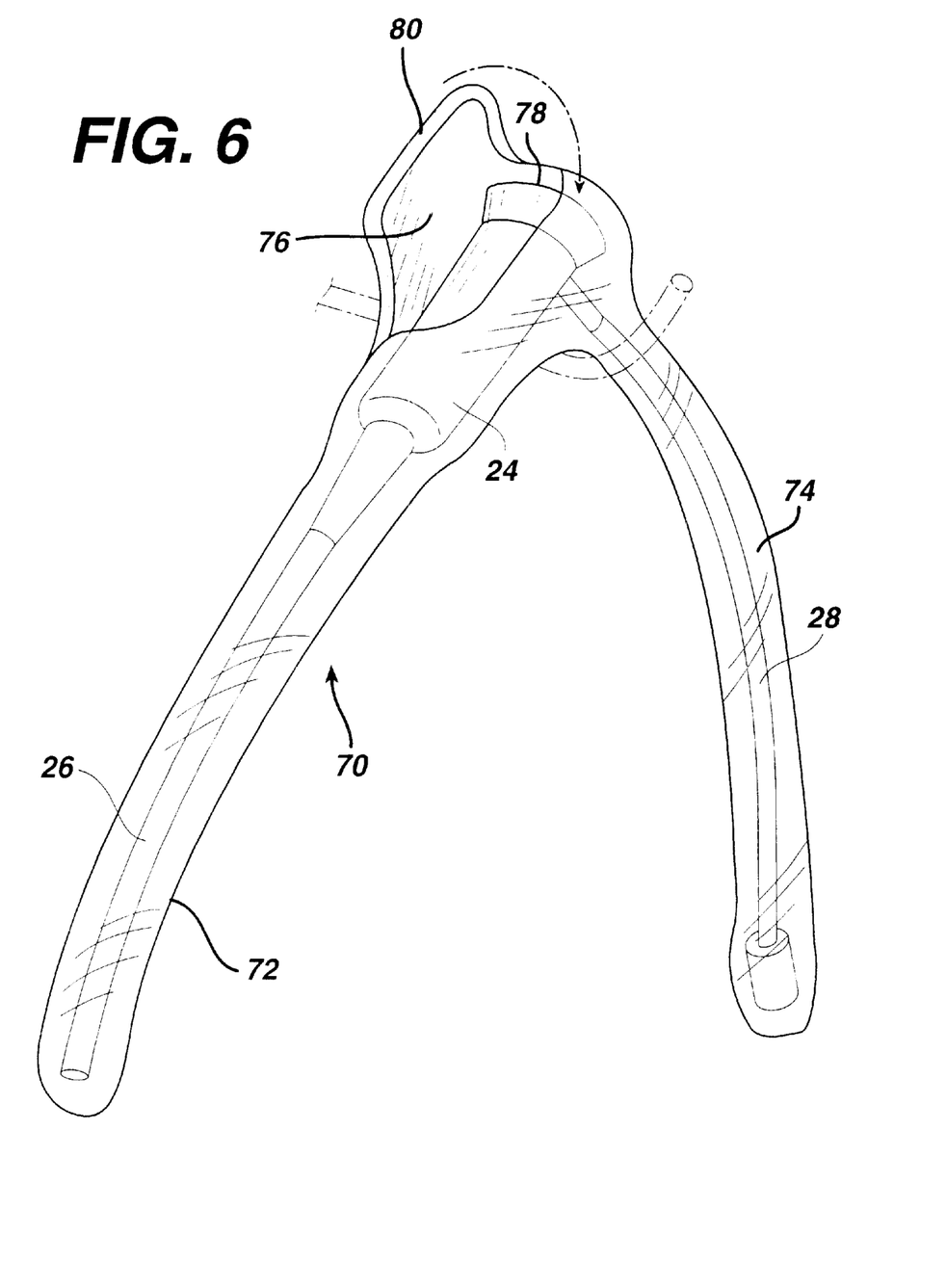
FIG. 6 is a perspective view of a fourth embodiment of a packaging enclosure according to the invention.

In a preferred embodiment shown in FIG. 6, a pouch 70 conforms closely to the shape of the endoscope 24, having a first portion 72 extending over and conforming to the first flexible tube 26 and a second portion 74 extending over and conforming to the second flexible tube. It is shown without the flat seals such as the seal 16 shown in FIG. 1, but such could be substituted. Preferably in the prior embodiments at least a portion of the seal 16 would completed by the user after inserting the endoscope 24. Such portion could be protected with a release liner over the adhesive prior to use. This embodiment illustrates such principle by having a flap 76 covering an opening 78 between the first and second portions 72 and 74 through which the endoscope 24 is inserted. After the endoscope 24 is inserted, the flap 76 is folded over the opening 78 and adhesive 80 thereon seals the endoscope 24 within the pouch.

Figure 7:
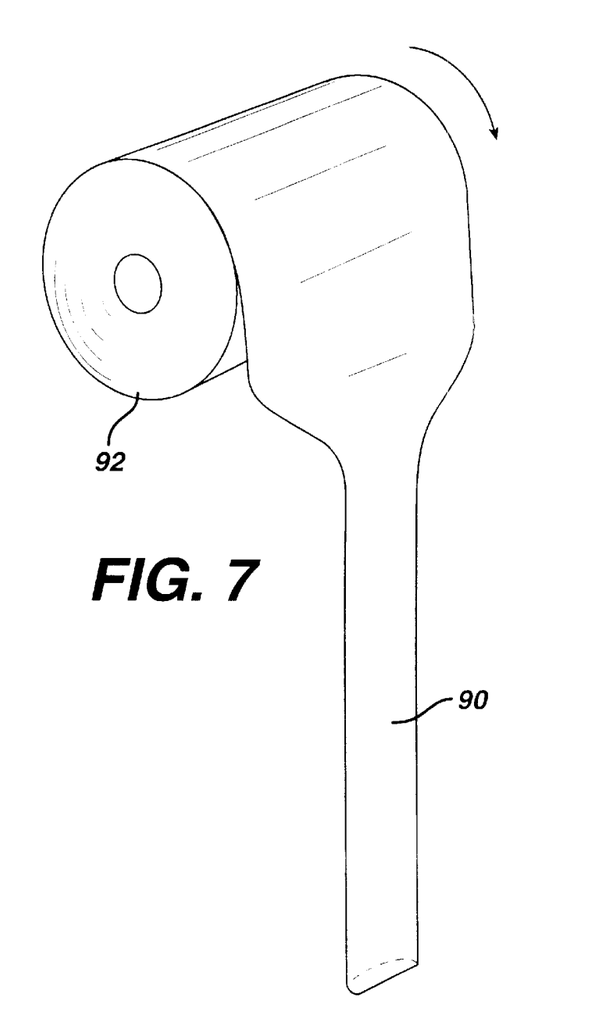
FIG. 7 is a perspective view of a roll of packaging enclosures, each of which comprise a fifth embodiment of the invention.
Figure 8:
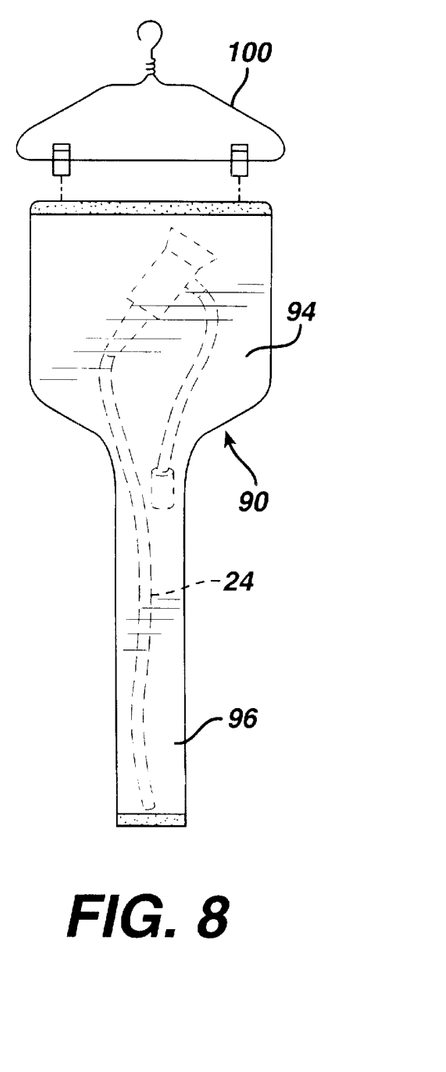
FIG. 8 is a front view of one of the packaging enclosures of FIG. 7.

FIGS. 7 and 8 show how pouches 90 according to the present invention may be provided on a convenient roll 92. Any of the prior embodiments could be so provided. The pouch 90 has a wider upper portion 94 for receiving the endoscope body 30 and a narrower lower portion 96 for receiving the flexible tubes 26 and 28. A hanger 100 such as the hanger 62 is provided.

Figure 9:
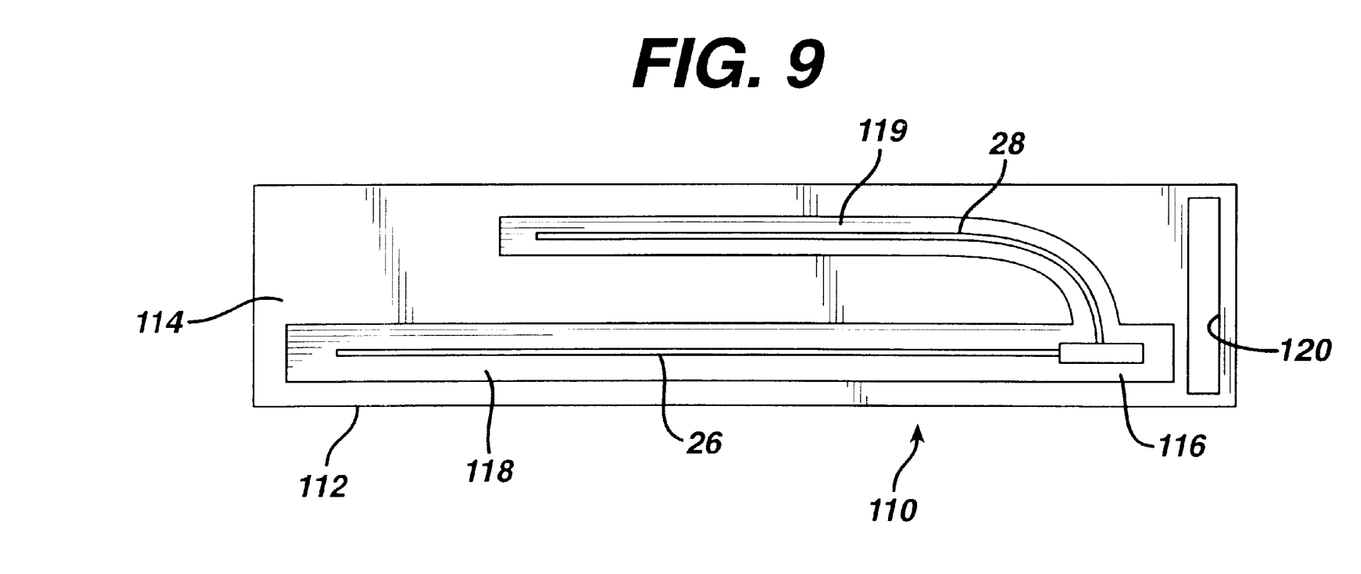
FIG. 9 is a top plan view of a sixth embodiment of a packaging enclosure according to the invention.
Figure 10:
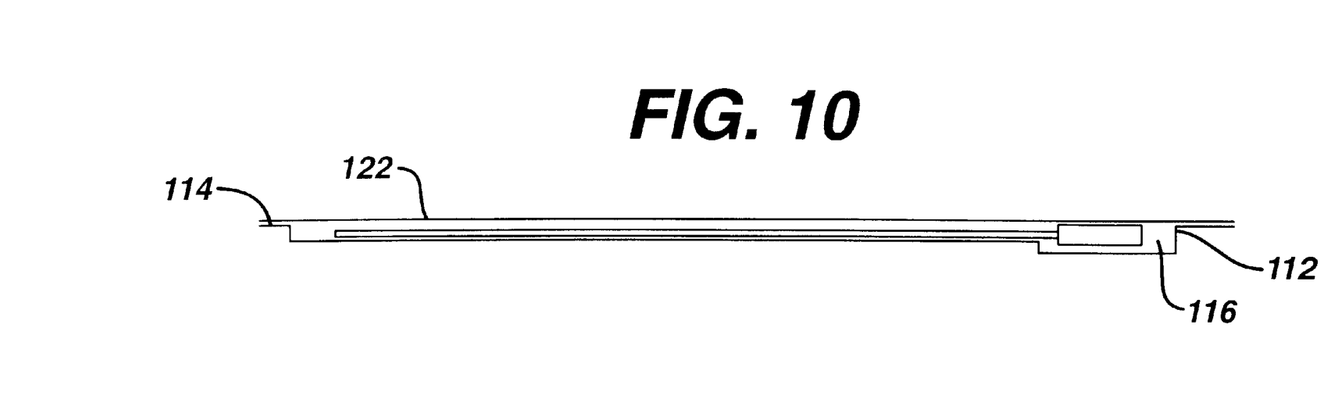
FIG. 10 is a side view of the embodiment of FIG. 9.
Figure 11:
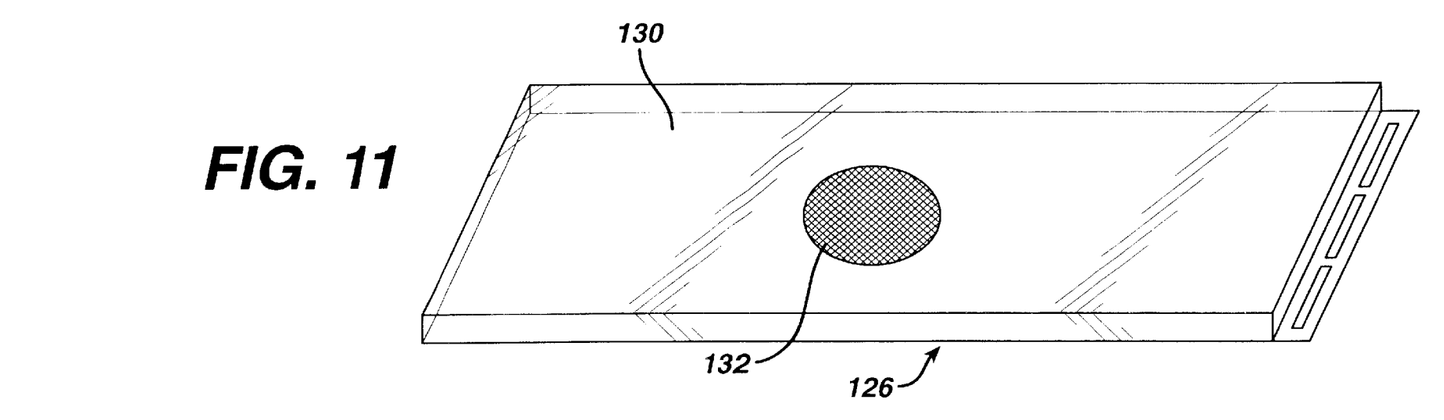
FIG. 11 is a perspective view showing the film of a seventh embodiment of a packaging enclosure according to the invention.

Other packaging designs may accomplish the same objectives. For instance, although pouches are convenient, one may desire to package the endoscope 24 within a more rigid container, yet nevertheless allow it to be draped over the hook 34. Preferably such a rigid structure would be polymer based, such as a thermoformed or cold formed plastic material as is generally used for sterile packaging of medical devices. FIGS. 9, 10 and 11 show a package 110 comprising a thermoformed base 112 having an upper surface 114 and a recess 116. The recess 116 is shaped to accommodate the endoscope 24 having a first portion 118 for receiving the first flexible tube 26 and a second portion 119 for receiving the second flexible tube 28. A hook receiving aperture 120 is provided for hanging the package with the endoscope 24 therein. A semi-permeable film 122 seals to the upper surface 114 of the base 112 to seal the endoscope 24 in the package to allow ingress of sterilizing gases yet impede ingress of contaminating microorganisms.

Figure 12:
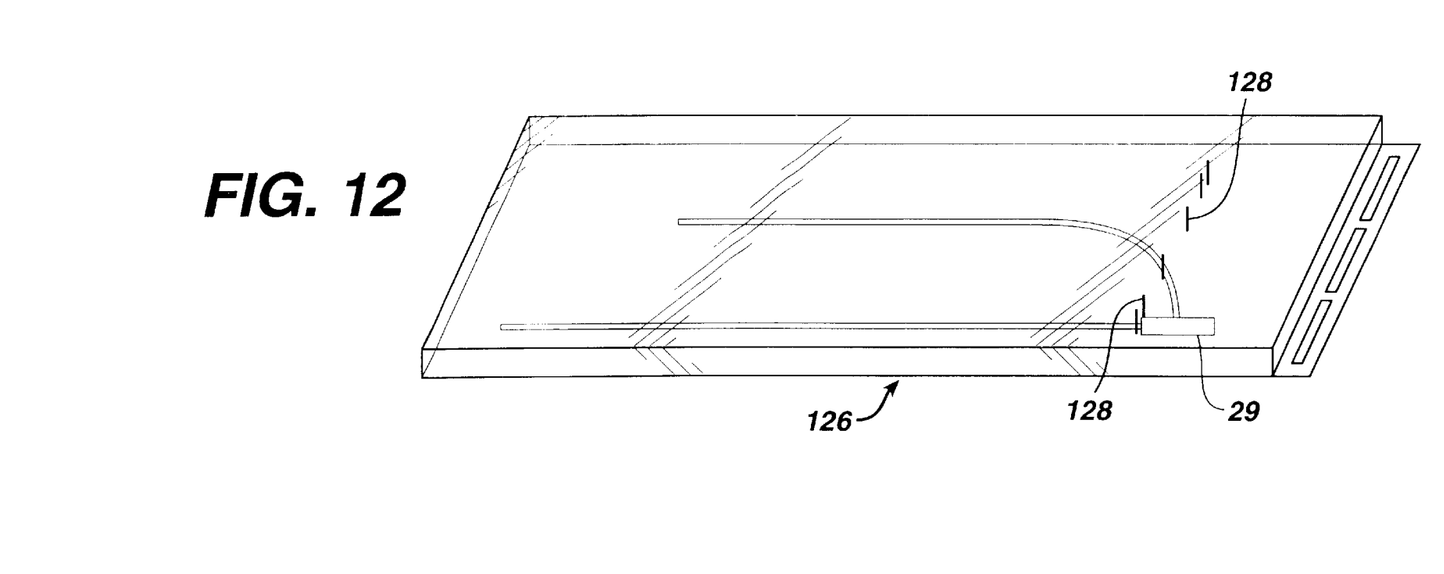
FIG. 12 is a perspective view of the embodiment of FIG. 11 with the film removed to show the interior construction.

FIGS. 11 and 12 show an alternative embodiment of a package 126 wherein rather than provide a shaped recess the package 126 has internal peg-like supports 128 formed therein and over which the endoscope 24 may be draped. Further a film 130 comprises a non-permeable substance with a window 132 of semi-permeable material to allow ingress of sterilizing gases. However, the film 122 could be formed entirely of a semi-permeable material.

Rather than sealing the endoscope 24 within a pouch prior to sterilization, the seal can be effected during the sterilization process, such as by drawing a vacuum in the sterilization environment which draws the adhesive opening closed. The effect could be enhanced by providing an inflatable ring around the opening which inflates under the vacuum to draw the adhesive edges closed.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method for sterilizing and storing an endoscope having first and second flexible tubes, said method comprising the steps of:

placing the endoscope within a packaging enclosure comprising a wall forming an interior space for receiving the endoscope, at least a portion of the wall being semi-permeable and wherein the first flexible tube is received within one portion of the packaging enclosure and the second flexible tube is received within a second portion of the packaging enclosure;

passing a sterilizing gas into the packaging enclosure; and hanging the packaging enclosure with the sterile endoscope therein over a member with the first flexible tube hanging to one side of the member and the second flexible tube hanging to the other side of the member.

2. A method according to claim 1 wherein the step of placing the endoscope within a the packaging enclosure comprises placing the endoscope within a pouch.

3. A method according to claim 1 wherein the step of placing the endoscope within the packaging enclosure comprises placing the endoscope within a sterile container with at least one semi-permeable port.

4. A method according to claim 1 wherein the step of hanging the package over the member comprises hanging the package over a hook.

5. A method for sterilizing and storing an endoscope having first and second flexible tubes, said method comprising the steps of:

placing the endoscope within a packaging enclosure comprising a wall forming an interior space for receiving the endoscope, at least a portion of the wall being semi-permeable;

passing a sterilizing gas into the packaging enclosure;

hanging the endoscope within the package over a support within the package with the first flexible tube hanging over one side of the support and the second flexible tube hanging over the other side of the support; and hanging the packaging enclosure with the sterile endoscope therein over a member via a hanger connected to the support.

6. A method according to claim 5 wherein the support is rigid, the hanger is rigid and the hanger rigidly connects to the support.

7. A method according to claim 6 wherein the step of placing the endoscope within the packaging enclosure comprises placing the endoscope within a rigid base, the support being a portion of the base and the endoscope being hung over the support within the base.

8. A method according to claim 6 wherein the step of placing the endoscope within the packaging enclosure comprises placing the endoscope within a thermoformed tray with a permeable lid stock, the support being a portion of the tray and the endoscope being hung over the support within the tray.

9. A method according to claim 6 wherein the hanger is a hook.

10. A method according to claim 9 wherein the hook is a closed loop.

* * * * *